(12) United States Patent
Matsushige et al.

(10) Patent No.: US 12,010,452 B2
(45) Date of Patent: Jun. 11, 2024

(54) ENDOSCOPIC DEVICE, DISPLAY IMAGE OUTPUT METHOD, COMPUTER-READABLE MEDIUM, AND ENDOSCOPIC SYSTEM

(71) Applicant: OLYMPUS CORPORATION, Hachioji (JP)

(72) Inventors: Ryunosuke Matsushige, Tokyo (JP); Hideyuki Wada, Tokyo (JP); Aki Matsumoto, Tokyo (JP); Takuya Ogura, Tokyo (JP); Satoru Ono, Tokyo (JP); Takahiro Yumoto, Tokyo (JP); Sachiko Hashimoto, Tokyo (JP); Tomomi Ouchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 119 days.

(21) Appl. No.: 17/736,455

(22) Filed: May 4, 2022

(65) Prior Publication Data

US 2022/0264031 A1 Aug. 18, 2022

Related U.S. Application Data

(63) Continuation of application No. PCT/JP2019/043245, filed on Nov. 5, 2019.

(51) Int. Cl.
*H04N 5/262* (2006.01)
*A61B 1/00* (2006.01)

(52) U.S. Cl.
CPC ....... *H04N 5/2628* (2013.01); *A61B 1/00045* (2013.01)

(58) Field of Classification Search
CPC ......... H04N 23/53; H04N 23/51; H04N 23/54
See application file for complete search history.

(56) References Cited

U.S. PATENT DOCUMENTS

| 2007/0078343 | A1* | 4/2007 | Kawashima | ........... A61B 8/463 |
| | | | | 600/443 |
| 2017/0049303 | A1* | 2/2017 | Kawano | ................. A61B 1/045 |
| 2018/0242818 | A1* | 8/2018 | Kubo | ...................... A61B 1/005 |
| 2020/0008653 | A1* | 1/2020 | Kamon | .............. A61B 1/00055 |

FOREIGN PATENT DOCUMENTS

| CN | 1874715 A | * 12/2006 | ......... A61B 1/00009 |
| JP | 2013-192803 A | 9/2013 | |

OTHER PUBLICATIONS

Feb. 10, 2020 International Search Report issued in International Patent Application No. PCT/JP2019/043245.

* cited by examiner

*Primary Examiner* — Michael Lee
(74) *Attorney, Agent, or Firm* — Oliff PLC

(57) ABSTRACT

An endoscopic device generates an endoscopic image based on an image pickup signal generated by an image pickup device at a distal-end portion of an insertion portion, acquires channel information regarding a channel formed in the insertion portion, acquires angle information regarding a display angle of the endoscopic image, and generates and outputs a display image including a display endoscopic image generated based on modifying the endoscopic image based on the angle information, and a channel guide image generated based on the angle information and the channel information.

20 Claims, 6 Drawing Sheets

ENDOSCOPIC DEVICE, DISPLAY IMAGE OUTPUT METHOD, COMPUTER-READABLE MEDIUM, AND ENDOSCOPIC SYSTEM

CROSS REFERENCE TO RELATED APPLICATIONS

This is a Continuation Application of PCT Application No. PCT/JP2019/043245, filed Nov. 5, 2019. The entire contents of which is incorporated herein.

BACKGROUND

Technical Field

The present description relates to an endoscopic device, a display image output method, a computer-readable medium, and an endoscopic system.

Description of the Related Art

Conventionally, known has been an endoscopic device that can generate an endoscopic image, on the basis of an image pickup signal generated by an endoscope, and can display the endoscopic image on a monitor. For example, known has been an endoscope including a channel that guides a treatment tool to a target region (treatment-tool channel). With such an endoscope, the surgical operator can treat a target region with a treatment tool while checking the treatment tool and the target region shown in the endoscopic image displayed on the monitor. The direction of entry of the treatment tool into the endoscopic image is determined due to the positional relationship between an objective lens at the distal-end face of the endoscope and the outlet of the treatment-tool channel. Note that the objective lens is part of an optical system that forms a subject image on an image pickup element at the distal-end portion of the endoscope.

Known has been an endoscopic system that prevents the surgical operator from feeling discomfort regarding the direction of entry of a treatment tool to an image). For example, the endoscopic system, when a user designates a direction for entry of a treatment tool into a display image displayed on a display (treatment-tool appearance direction), at least enlarges or reduces a processing image and creates a rotated and enlarged image such that the treatment tool appears from the treatment-tool appearance direction.

SUMMARY

According to one aspect provided is an endoscopic device including a processor configured to: generate an endoscopic image based on an image pickup signal generated by an image pickup device at a distal-end portion of an insertion portion, acquire channel information regarding a channel formed in the insertion portion, acquire angle information regarding a display angle of the endoscopic image, and generate and output a display image including a display endoscopic image generated by modifying the endoscopic image based on the angle information, and a channel guide image generated based on the angle information and the channel information.

According to another aspect provided is a display image output method including: generating an endoscopic image based on an image pickup signal generated by an image pickup device at a distal-end portion of an insertion portion, acquiring channel information regarding a channel formed in the insertion portion, acquiring angle information regarding a display angle of the endoscopic image, and generating and outputting a display image including a display endoscopic image generated by modifying the endoscopic image based on the angle information, and a channel guide image generated on based on the angle information and the channel information.

According to another aspect provided is a non-transitory computer-readable storage medium storing a computer executable program for causing a computer to perform processing comprising: generating an endoscopic image based on an image pickup signal generated by an image pickup device at a distal-end portion of an insertion portion, acquiring channel information regarding a channel formed in the insertion portion, acquiring angle information regarding a display angle of the endoscopic image, and generating and outputting a display image including a display endoscopic image generated by modifying the endoscopic image based on the angle information, and a channel guide image generated based on the angle information and the channel information.

According to another aspect provided is an endoscopic system including: an endoscope including: an insertion portion, an image pickup device at a distal-end portion of the insertion portion, a channel formed in the insertion portion, and a memory storing channel information regarding the channel; and an endoscopic device including a processor configured to: generate an endoscopic image based on an image pickup signal output from the image pickup device, acquire the channel information, acquire angle information regarding a display angle of the endoscopic image, and generate and output a display image including a display endoscopic image generated by modifying the endoscopic image based on the angle information, and a channel guide image generated based on the angle information and the channel information.

DESCRIPTION OF THE EMBODIMENTS

In an endoscopic device having a function of rotating an endoscopic image to be displayed on a monitor, in accordance with an instruction from the surgical operator, the direction of entry of a treatment tool into the endoscopic image varies along with rotation of the endoscopic image. Thus, for example, with an endoscope having a plurality of channels, the surgical operator has difficulty promptly grasping the direction of entry of the treatment tool into the endoscopic image.

An embodiment of the present invention will be described below with reference to the drawings.

Figure 1:
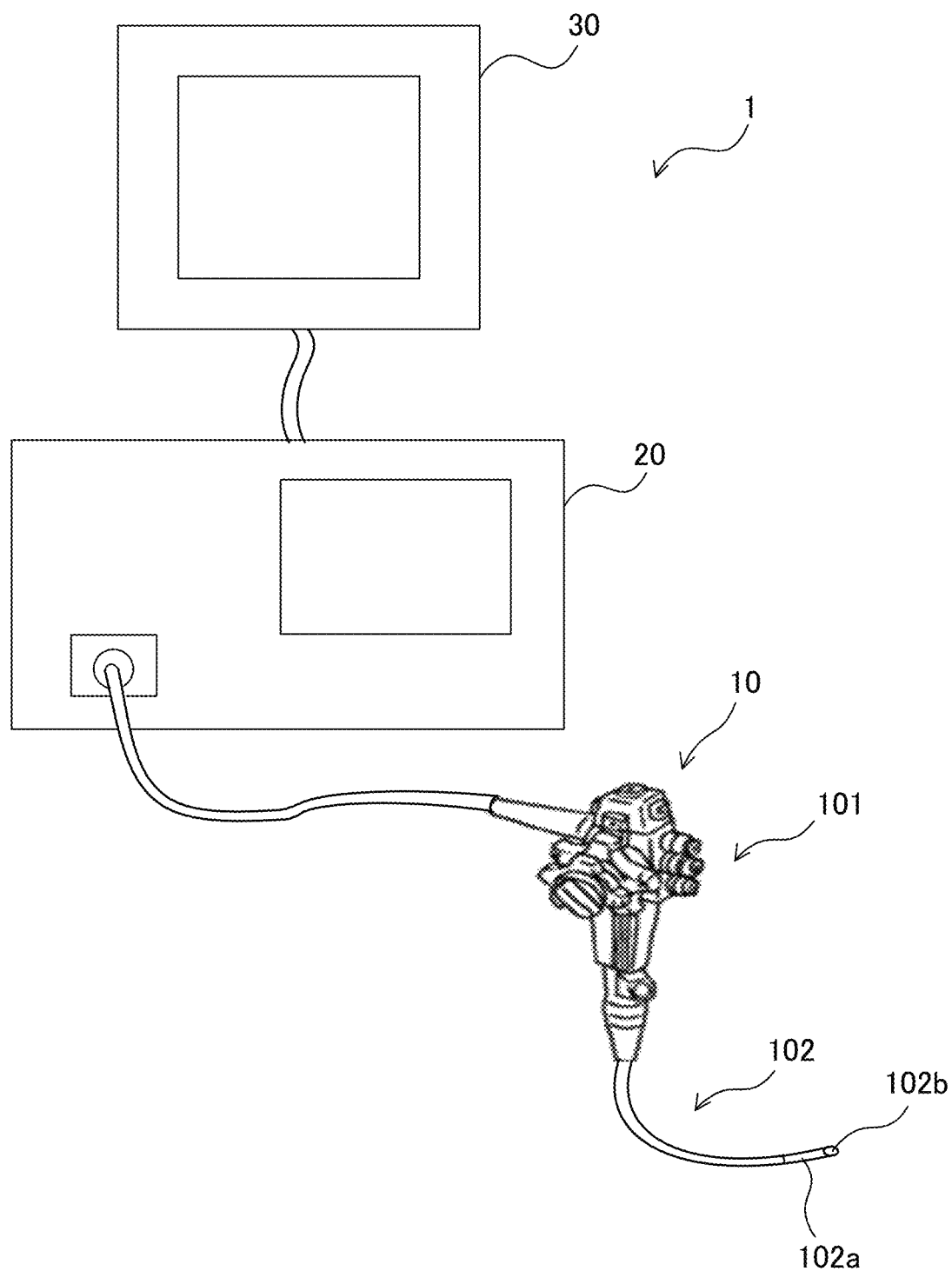
FIG. 1 is a diagram illustrating the configuration of an endoscopic system including an endoscopic device according to an embodiment.

FIG. 1 illustrates the configuration of an endoscopic system including an endoscopic device according to the embodiment.

The endoscopic system 1 illustrated in FIG. 1 includes an endoscope 10 and a display device 30 in addition to the endoscopic device 20, in which the endoscope 10 and the display device 30 are in connection with the endoscopic device 20. In the present embodiment, transmission and reception of signals (data or information) are performed by wire between the endoscope 10 and the endoscopic device 20 and between the endoscopic device 20 and the display device 30, but may be performed by wireless.

The endoscope 10 serves as a flexible endoscope and includes an operation unit 101 that the surgical operator operates and an insertion portion 102 to be inserted into the body of a patient.

The operation unit 101 includes operation members with which the surgical operator controls the endoscope 10, such as an angle knob for controlling the insertion portion 102 to bend upward, downward, leftward, or rightward, an air/water supply button for controlling air supply and water supply, and a suction button for controlling suction. The operation unit 101 further includes a channel inlet through which a treatment tool is inserted (e.g., a forceps inlet) and an operation member for giving an instruction to the endoscopic device 20.

The insertion portion 102 has a plurality of channels (conduits) formed inside. Examples of the plurality of channels include a treatment-tool channel, an air/water supply channel, and a suction channel. The insertion portion 102 has, at its distal-end portion 102a, for example, an image pickup unit including an image pickup element (image pickup unit 103 to be described below) and an optical system that forms a subject image on the image pickup element. The insertion portion 102 has, at its distal-end face 102b, for example, a plurality of channel outlets and an objective lens. Note that the objective lens is part of the optical system that forms a subject image on the image pickup element.

The endoscopic device 20 generates an endoscopic image, on the basis of an image pickup signal generated by the image pickup unit in the endoscope 10. The endoscopic device 20 performs, for example, generation of a display endoscopic image resulting from rotation of the endoscopic image based on an instruction for endoscopic-image rotation from the surgical operator or the like, generation of a channel guide image as a guide for the outlet position (outlet direction) of a channel, generation of a display image including the display endoscopic image and the channel guide image, and output of the display image. Note that such an instruction for endoscopic-image rotation from the surgical operator or the like corresponds to an instruction for display of an endoscopic image to be displayed on the display device 30, through rotation by a desired angle, and can be given by an operation to the operation unit 101 in the endoscope 10 or by an operation to an operation unit (operation unit 202 to be described below) in the endoscopic device 20. In this case, the surgical operator or the like may be allowed to designate any angle or may be allowed to select and designate an angle from a plurality of different angles.

The display device 30 is, for example, a liquid-crystal display device and displays, for example, a display image output from the endoscopic device 20.

Figure 2:
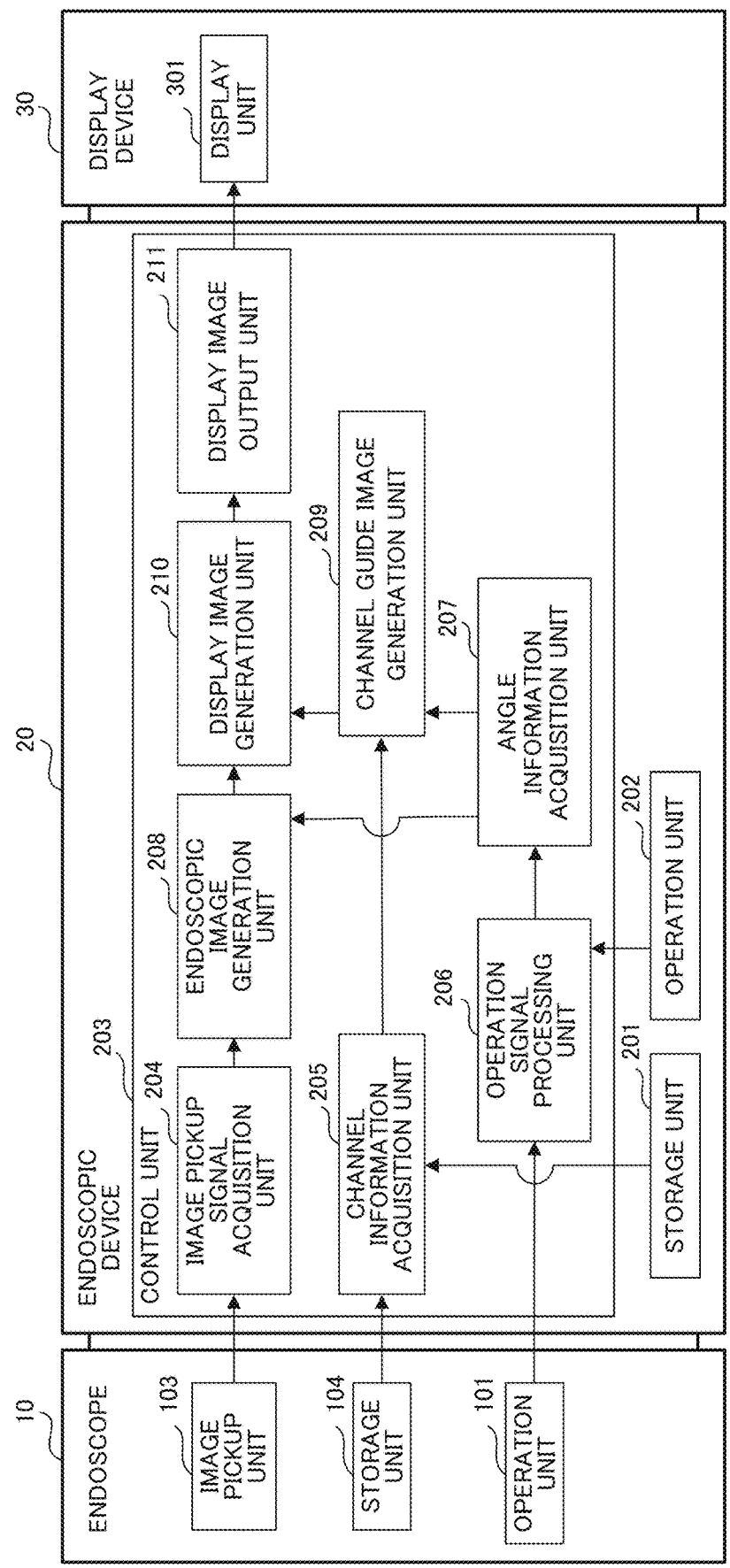
FIG. 2 is a diagram illustrating the functional configuration related to display of a display image in the endoscopic system.

FIG. 2 illustrates the functional configuration related to display of a display image in the endoscopic system 1.

In the endoscopic system 1 illustrated in FIG. 2, the endoscope 10 includes a storage unit 104 in addition to the operation unit 101 and the image pickup unit 103.

As described above, for example, in response to an operation for an instruction to the endoscopic device 20, the operation unit 101 outputs, to the endoscopic device 20, a signal (operation signal) corresponding to the operation.

The image pickup unit 103 includes a signal processing unit in addition to the image pickup element. The image pickup element is, for example, a charge coupled device (CCD) and converts, into an electric signal, the subject image formed by the optical system including the objective lens. The signal processing unit performs predetermined signal processing, such as gain adjustment processing and analog-to-digital (AD) conversion processing, to the electric signal resulting from the conversion by the image pickup element, to generate an image pickup signal. Note that the signal processing unit may be achieved, for example, by a circuit. In this case, the image pickup unit 103 may be provided as an image pickup circuit including an image pickup element and a signal processing circuit.

The storage unit 104 serves as a nonvolatile memory storing information regarding the endoscope 10. The information regarding the endoscope 10 includes classification information on the endoscope 10 and channel information regarding the channels formed in the insertion portion 102. The channel information includes information regarding the angle of outlet position (outlet direction) of each channel when the display angle (rotation angle) of the endoscopic image is a predetermined angle or the channel guide image when the display angle of the endoscopic image is the predetermined angle. Here, the predetermined angle is any of an angle of 0° and a plurality of different angles. A specific example of the channel information will be given below.

The endoscopic device 20 includes a storage unit 201 and a control unit 203 in addition to the operation unit 202.

The storage unit 201 serves as a nonvolatile memory storing various types of information to be read out by the control unit 203 as necessary. The various types of information include the channel information regarding the channels formed in the insertion portion 102 of the endoscope 10 or respective pieces of channel information on endoscopes different in classification.

The operation unit 202 is, for example, an operation panel or a touch panel. The operation unit 202 receives an input operation from a user and outputs, to the control unit 203, a signal (operation signal) corresponding to the input operation.

The control unit 203 controls the entire operation of the endoscopic device 20. The control unit 203 includes an image pickup signal acquisition unit 204, a channel information acquisition unit 205, an operation signal processing unit 206, an angle information acquisition unit 207, an endoscopic image generation unit 208, a channel guide image generation unit 209, a display image generation unit 210, and a display image output unit 211.

The image pickup signal acquisition unit 204 acquires the image pickup signal generated by the image pickup unit 103 of the endoscope 10.

The channel information acquisition unit 205 acquires the channel information regarding the channels formed in the insertion portion 102 of the endoscope 10. For example, the channel information acquisition unit 205 may acquire the channel information from the storage unit 104 of the endoscope 10 or from the storage unit 201. For example, for acquisition from the storage unit 201, the channel information acquisition unit 205 may acquire the classification information on the endoscope 10 from the storage unit 104 of the endoscope 10 and acquire the channel information corresponding to the classification information from the storage unit 201. For example, the channel information acquisition unit 205 may acquire the channel information from a server (not illustrated) connected to the endoscopic device 20 through a network. In this case, for example, the channel information acquisition unit 205 may acquire the classification information on the endoscope 10 from the storage unit 104 of the endoscope 10, inquire of the server the channel information corresponding to the classification information, and acquire the channel information. Thus, for example, solved can be a problem that retention of channel information in the endoscopic device 20 makes a new endoscope difficult to deal with or solved can be a problem that an endoscope needs a reduction in function for achievement of an inexpensive endoscope.

The operation signal processing unit 206 receives the operation signal output from the operation unit 101 of the endoscope 10 or the operation signal output from the operation unit 202, and performs processing corresponding to the operation signal. For example, in a case where the received operation signal corresponds to an operation signal related to an instruction for endoscopic-image rotation, the operation signal processing unit 206 outputs, to the angle information acquisition unit 207, angle information regarding the rotation angle (display angle) of the endoscopic image that the instruction indicates.

The angle information acquisition unit 207 acquires the angle information output from the operation signal processing unit 206.

The endoscopic image generation unit 208 generates an endoscopic image, on the basis of the image pickup signal acquired by the image pickup signal acquisition unit 204. The endoscopic image generation unit 208 also generates a display endoscopic image, on the basis of the generated endoscopic image and the angle information acquired by the angle information acquisition unit 207. The display endoscopic image corresponds to an image resulting from rotation of the endoscopic image by the display angle that the angle information indicates. Note that, in a case where the angle information acquisition unit 207 has acquired no angle information, the generated endoscopic image is provided as the display endoscopic image.

The channel guide image generation unit 209 generates a channel guide image, on the basis of the channel information acquired by the channel information acquisition unit 205 and the angle information acquired by the angle information acquisition unit 207. The channel guide image corresponds to an image serving as a guide for the outlet position (outlet direction) of each channel when the display angle of the endoscopic image is the display angle that the angle information indicates. Note that, in a case where the angle information acquisition unit 207 has acquired no angle information, with a display angle of 0° as angle information, a channel guide image is generated.

The display image generation unit 210 generates a display image including the display endoscopic image generated by the endoscopic image generation unit 208 and the channel guide image generated by the channel guide image generation unit 209.

The display image output unit 211 outputs, to the display device 30, the display image generated by the display image generation unit 210.

The display device 30 includes a display unit 301 that displays, for example, the display image output from the display image output unit 211 of the endoscopic device 20.

Here, a specific example of the channel information described above will be given.

Note that, in the specific example, the number of channels formed in the insertion portion 102 of the endoscope 10 is two. Due to the positional relationship between two channel outlets and the objective lens at the distal-end face 102b of the insertion portion 102, the directions of entry of treatment tools or the like from the two channel outlets into the display endoscopic image as the endoscopic image displayed at a display angle of 0° on the display device 30 are the direction at 90° (direction from right) and the direction at 225° (direction from lower left). Note that, in the specific example, the directions at 0°, 90°, 180°, and 270° are the directions from above, right, below, and left, respectively.

In this case, for example, the channel information may include information regarding the angles (90° and 225°) of positions of the two channel outlets when the display angle of the endoscopic image is 0°. Alternatively, for example, the channel information may include the information regarding the angles (90° and 225°) of positions of the two channel outlets when the display angle of the endoscopic image is 0° and information regarding the angles (270° and 45°) of positions of the two channel outlets when the display angle of the endoscopic image is 180°. As above, the channel information may include information regarding the angles of outlet positions of the channels when a single predetermined angle or a plurality of predetermined angles is provided as the display angle of the endoscopic image.

For example, the channel information may include the channel guide image when the display angle of the endoscopic image is 0°. Alternatively, for example, the channel information may include the channel guide image when the display angle of the endoscopic image is 0° and the channel guide image when the display angle of the endoscopic image is 180°. As above, the channel information may include the channel guide image when a single predetermined angle is provided as the display angle of the endoscopic image or the channel guide images when a plurality of predetermined angles is provided as the display angle of the endoscopic image.

Figure 3:
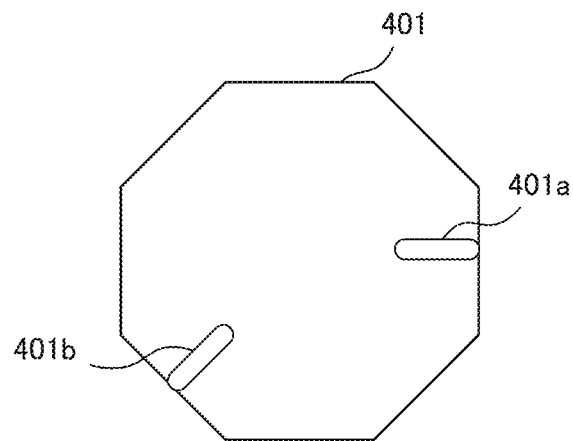
FIG. 3 is a diagram illustrating channel guide images included in channel information.
Figure 3:
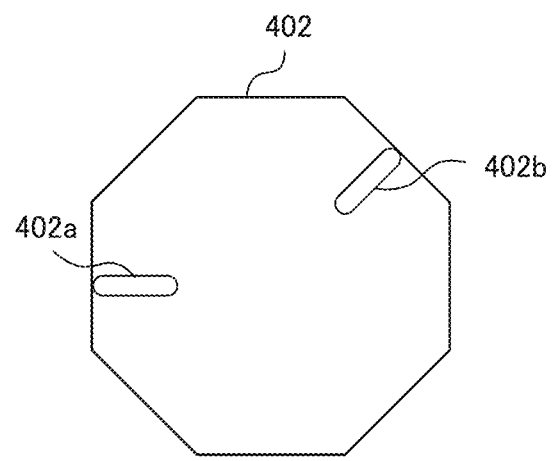

FIG. 3 illustrates channel guide images included in the channel information.

Referring to FIG. 3, a channel guide image 401 corresponds to the channel guide image when the display angle of the endoscopic image is 0°, and a channel guide image 402 corresponds to the channel guide image when the display angle of the endoscopic image is 180°. Guides 401a and 401b in the channel guide image 401 serve as guides for the outlet positions of the channels when the display angle of the endoscopic image is 0°. Guides 402a and 402b in the channel guide image 402 serve as guides for the outlet positions of the channels when the display angle of the endoscopic image is 180°.

Figure 4:
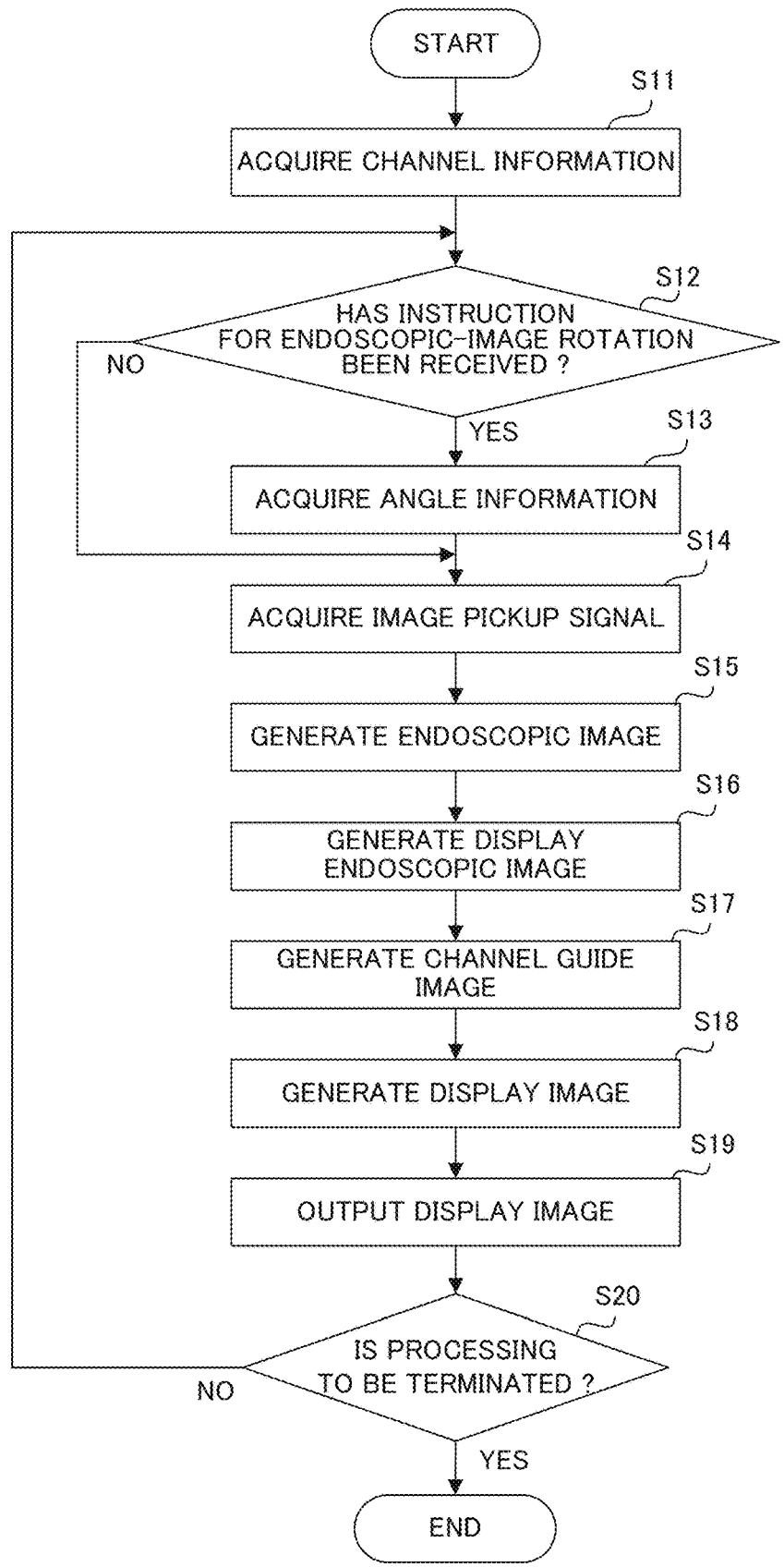
FIG. 4 is a flowchart of display image output processing that is performed in the endoscopic device according to the embodiment.

FIG. 4 is a flowchart of display image output processing that is performed in the endoscopic device 20. The display image output processing is achieved with the functional configuration of the endoscopic device 20 illustrated in FIG. 2.

When the display image output processing illustrated in FIG. 4 starts, first, the channel information acquisition unit 205 acquires, from the storage unit 104 of the endoscope 10 or the storage unit 201, the channel information regarding the channels formed in the insertion portion 102 of the endoscope 10 (S11).

Next, the control unit 203 determines whether or not an instruction for endoscopic-image rotation has been received from the surgical operator or the like (S12). For example, the determination is performed on the basis of whether or not an operation signal related to the instruction for endoscopic-image rotation has been input to the operation signal processing unit 206.

In a case where the determination in S12 results in YES, the operation signal processing unit 206 outputs, to the angle information acquisition unit 207, angle information regarding the rotation angle (display angle) of the endoscopic image indicated by the instruction for endoscopic-image rotation to which the input operation signal is related, so that the angle information acquisition unit 207 acquires the angle information (S13).

After S13 or in a case where the determination in S12 results in NO, the image pickup signal acquisition unit 204 acquires the image pickup signal generated by the image pickup unit 103 of the endoscope 10 (S14).

Next, the endoscopic image generation unit 208 generates an endoscopic image, on the basis of the image pickup signal acquired in S14 (S15), and then generates a display endoscopic image, on the basis of the endoscopic image and the latest angle information acquired in S13 (latest angle information acquired in S13 after the display image output processing starts) (S16). Note that, in a case where no processing has been performed in S13 after the display image output processing starts, the endoscopic image generated in S15 is provided as the display endoscopic image.

Next, the channel guide image generation unit 209 generates a channel guide image, on the basis of the channel information acquired in S11 and the latest angle information acquired in S13 (S17). Note that, in a case where no processing has been performed in S13 after the display image output processing starts, with a display angle of 0° as the latest angle information, a channel guide image is generated.

Next, the display image generation unit 210 generates a display image including the display endoscopic image generated in S16 and the channel guide image generated in S17 (S18).

Next, the display image output unit 211 outputs, to the display device 30, the display image generated in S18 (S19). When the display device 30 receives the display image output from the endoscopic device 20 in S19, the display unit 301 displays the display image. Thus, displayed is the display image including the display endoscopic image and the channel guide image.

Next, the control unit 203 determines whether or not the processing is to be terminated (S20). For example, the determination is performed on the basis of whether or not an operation signal related to an instruction for powering off the endoscopic device 20 has been input to the operation signal processing unit 206.

In a case where the determination in S20 results in NO, the processing goes back to S12. In a case where the determination in S20 results in YES, the display image output processing terminates.

Figure 5:
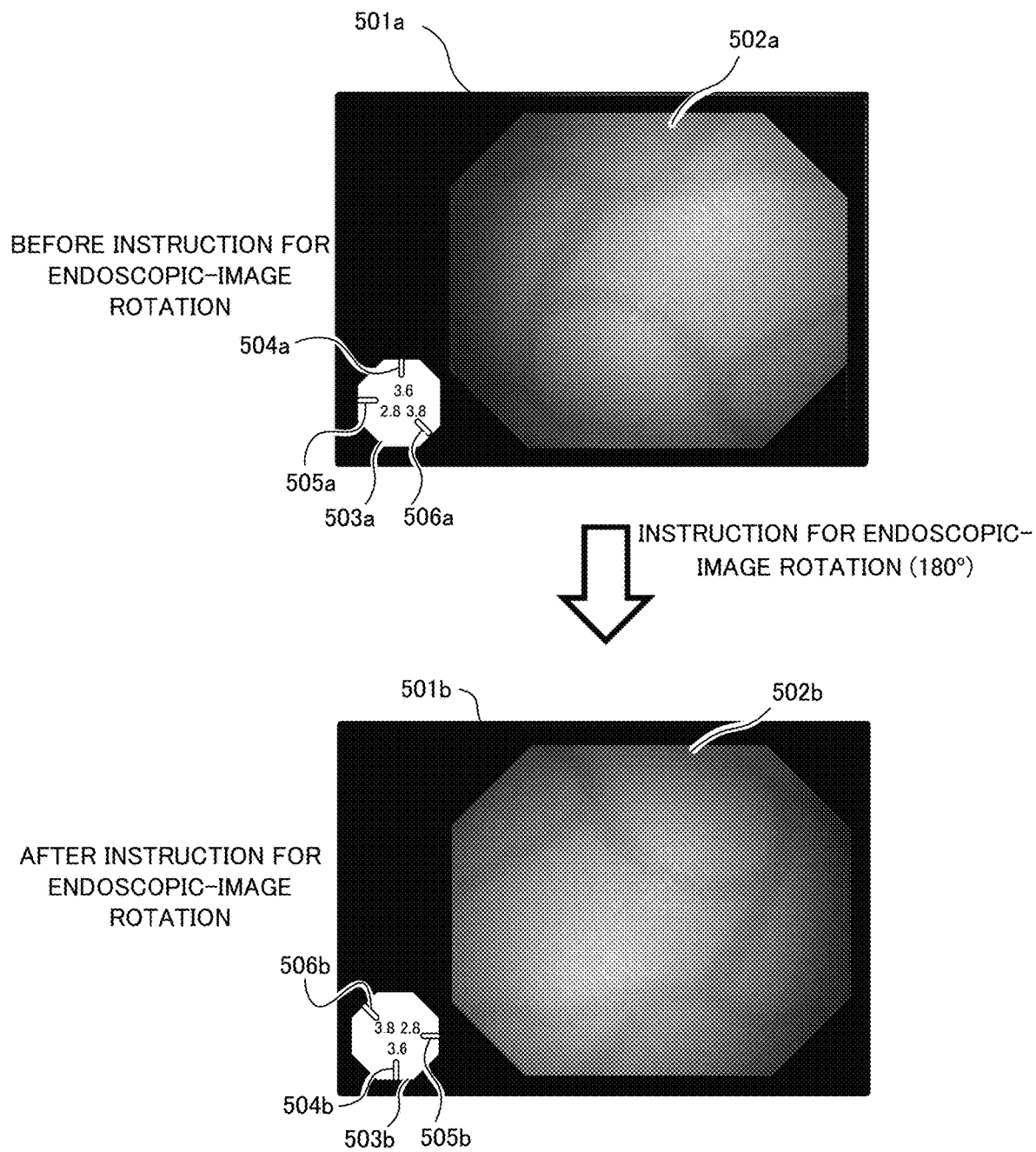
FIG. 5 is a diagram illustrating display images before and after an instruction for endoscopic-image rotation, displayed on a display device after output due to the display image output processing illustrated in FIG. 4.

FIG. 5 illustrates display images before and after an instruction for endoscopic-image rotation, displayed on the display device 30 after output due to the display image output processing illustrated in FIG. 4.

In this example, the insertion portion 102 of the endoscope 10 has three channels formed therein. As an instruction for endoscopic-image rotation, given is an instruction for a rotation of 180° of the endoscopic image (display through rotation).

Referring to FIG. 5, a display image 501a illustrated on the upper side corresponds to the display image before the instruction for endoscopic-image rotation, and includes a display endoscopic image (endoscopic image at a display angle of 0°) 502a and a channel guide image 503a. Guides 504a, 505a, and 506a in the channel guide image 503a serve as guides for the outlet positions of the channels at a point in time before the instruction for endoscopic-image rotation (when the display angle of the endoscopic image is 0°).

A display image 501b illustrated on the lower side corresponds to the display image after the instruction for endoscopic-image rotation, and includes a display endoscopic image (endoscopic image at a display angle of) 180° 502b and a channel guide image 503b. Guides 504b, 505b, and 506b in the channel guide image 503b serve as guides for the outlet positions of the channels at a point in time after the instruction for endoscopic-image rotation (when the display angle of the endoscopic image is 180°).

As illustrated in FIG. 5, in response to the instruction for endoscopic-image rotation, the display endoscopic image 502 is displayed through a rotation of 180° and additionally the positions of the guides 504, 505, and 506 in the channel guide image 503 are changed. Note that three numerical values in the channel guide image 503 indicate the diameters of three channel outlets. Information regarding the diameters of the channel outlets is included, for example, in the channel information described above.

Thus, while checking the channel guide image 503, the surgical operator can grasp the outlet positions of the channels not only before the instruction for endoscopic-image rotation but also after the instruction for endoscopic-image rotation. For example, in a case where the channel with the diameter "3.6" corresponds to a channel for treatment tool A, before the instruction for endoscopic-image rotation, the surgical operator can easily grasp that the direction of entry of the treatment tool A into the display endoscopic image 502a is the direction from above. After the instruction for endoscopic-image rotation, the surgical operator can easily grasp that the direction of entry of the treatment tool A into the display endoscopic image 502b is the direction from below.

Note that the display image displayed on the display device 30 after generated by the endoscopic device 20 is not limited to the form illustrated in FIG. 5.

For example, the display image may further include an endoscopic information window that displays the information regarding the endoscope 10 (e.g., name and model number), and the channel guide image may be displayed in the endoscopic information window. In this case, as long as the endoscopic image has been displayed through rotation, an icon indicating that the endoscopic image has been displayed through rotation may be displayed additionally in the endoscopic information window, and the icon itself may be displayed through rotation so as to match the rotation angle of the endoscopic image. Such an endoscopic information window may be displayed so as not to overlap the display endoscopic image.

For example, the display image may further include a channel information window that displays the channel information, and the channel guide image may be displayed in the channel information window. In this case, as long as the endoscopic image has been displayed through rotation, an icon indicating that the endoscopic image has been displayed through rotation may be displayed additionally in the channel information window, and the icon itself may be displayed through rotation so as to match the rotation angle of the endoscopic image. Such a channel information window may be displayed in superimposition on the display endoscopic image as long as observation is not interrupted.

For example, the display image may include such an endoscopic information window and a channel information window as above. In this case, for example, for display of the channel information window, in accordance with an instruction for setting from the surgical operator or the like, any of full-time display, two-second display, and no display may be selected.

Note that, in the display image described above, the shape of the display endoscopic image is not limited to an octagon and thus may be, for example, a circle. In this case, the shape of the channel guide image may be a circle.

As above, according to the present embodiment, even in a case where the endoscopic image to be displayed on the display device 30 is rotated in accordance with an instruction from the surgical operator or the like, the surgical operator or the like can easily grasp the direction of entry of a treatment tool or the like into the endoscopic image.

Note that, in the present embodiment, the control unit 203 of the endoscopic device 20 may be achieved by an integrated circuit, such as an application specific integrated circuit (ASIC) or a field programmable gate array (FPGA).

Figure 6:
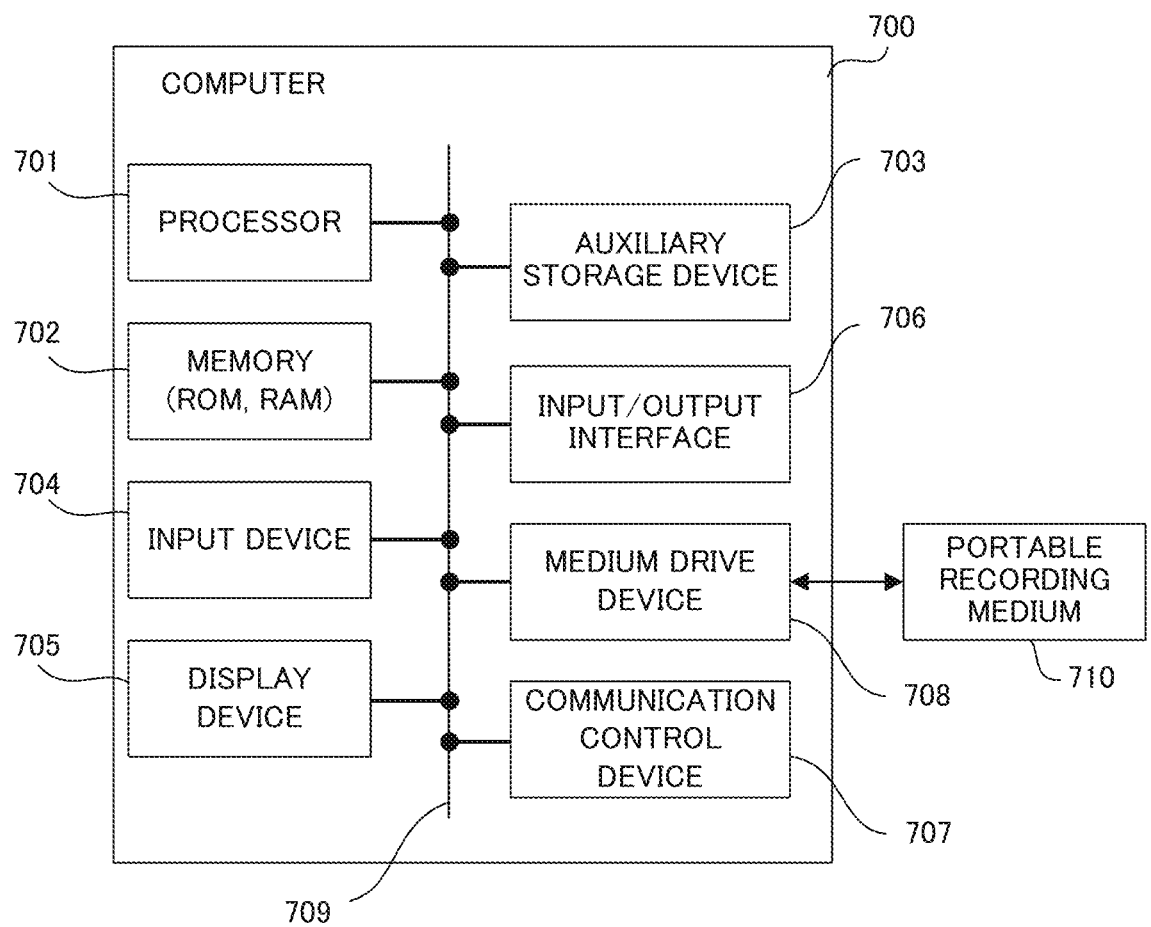
FIG. 6 is a diagram illustrating the hardware configuration of a computer.

For example, the storage unit 201, the operation unit 202, and the control unit 203 of the endoscopic device 20 may be achieved by a computer having such a hardware configuration as illustrated in FIG. 6.

FIG. 6 illustrates the hardware configuration of a computer.

As illustrated in FIG. 6, the computer 700 includes a processor 701, such as a central processing unit (CPU), a memory 702, an auxiliary storage device 703, an input device 704, a display device 705, an input/output interface 706, a communication control device 707, and a medium drive device 708. The elements 701 to 708 in the computer 700 are mutually connected through a bus 709, enabling transmission and reception of data between elements.

The processor 701 executes a program to control the entire operation of the computer 700. For example, the processor 701 executes a program for achieving the function of the control unit 203 illustrated in FIG. 2. Thus, for example, the display image output processing illustrated in FIG. 4 is performed.

The memory 702 includes a read only memory (ROM) and a random access memory (RAM) not illustrated. The ROM of the memory 702 has, for example, a program to be executed by the processor 701, in advance stored therein. The ROM of the memory 702 can be used as a storage for the program for achieving the function of the control unit 203 illustrated in FIG. 2. The RAM of the memory 702 is used, for example, as a work area for the processor 701.

For example, the auxiliary storage device 703 is a magnetic disk, such as a hard disk drive (HDD), or a nonvolatile memory, such as a flash memory. The auxiliary storage device 703 can store, for example, a program to be executed by the processor 701. The auxiliary storage device 703 can be used as a storage for the program for achieving the function of the control unit 203 illustrated in FIG. 2.

The input device 704 includes, for example, a key board, a mouse, and a touch panel. When an operator makes a predetermined operation to the input device 704 of the computer 700, the input device 704 transmits, to the processor 701, input information associated with the details of the operation. The input device 704 can be used as the operation unit 202.

The display device 705 is, for example, a liquid-crystal display device. The display device 705 can be used as the display device 30.

The input/output interface 706 connects the computer 700 to an electronic component or external apparatus. The input/output interface 706 can be used in order to establish connection with the endoscope 10 or the display device 30.

The communication control device 707 connects the computer 700 to a network and controls various types of communication between the computer 700 and an external device (e.g., a server) through the network. The communication control device 707 can be used in order to connect the endoscopic device 20 to a network and control various types of communication between the endoscopic device 20 and a server through the network.

The medium drive device 708 reads out a program or data stored in a portable recording medium 710 or writes data or the like stored in the auxiliary storage device 703 into the portable recording medium 710. The portable recording medium 710 can be used as a storage for the program for achieving the function of the control unit 203 illustrated in FIG. 2. An example of the portable recording medium 710 is a secure digital (SD) memory card (flash memory). In a case where the computer 700 is equipped with an optical disc drive available as the medium drive device 708, various types of optical discs that the optical disc drive can recognize can be used as the portable recording medium 710. Examples of optical discs available as the portable recording medium 710 include a compact disc (CD), a digital versatile disc (DVD), and a Blu-ray disc (Blu-ray is a registered trademark).

In the present embodiment, the endoscopic system 1 is not limited to the form illustrated in FIG. 1. Thus, like a so-called portable flexible endoscope, the endoscope 10, the endoscopic device 20, and the display device 30 may be integrated together. In the endoscopic system 1, the endoscope 10 and the endoscopic device 20 may be integrated together or the endoscopic device 20 and the display device 30 may be integrated together. In the endoscopic system 1, the endoscopic device 20 may be achieved by a computer (e.g., a server) connected to a network. The endoscope 10 and the endoscopic device 20 may be connected through the network and the endoscopic device 20 and the display device 30 may be connected through the network.

The embodiment has been described above, but the present invention is not limited to the above embodiment. Thus, embodiments can be made with modification of constituent elements without departing from the gist of the invention. Various modifications can be made with any appropriate combinations of a plurality of constituent elements disclosed in the above embodiment. For example, some constituent elements may be omitted from the constituent elements described in the embodiment.

What is claimed is:

1. An endoscopic device comprising:
   a processor configured to:
      generate an endoscopic image;
      acquire channel information regarding each of at least two channels formed in an insertion portion of an endoscope;
      acquire angle information regarding a display angle of the endoscopic image;
      generate a display endoscopic image by modifying the endoscopic image based on the angle information;

generate a channel guide image separate from the endoscopic image based on both the angle information and the channel information; and generate and output a display image including both the display endoscopic and the channel guide image, wherein the channel information includes information regarding angles of positions of channel outlets of respective ones of the two channels or of the channel guide image when the display angle of the endoscopic image is 0°, and/or information regarding angles of positions of the channel outlets or of the channel guide image when the display angle of the endoscopic image is 180°.

2. The endoscopic device according to claim 1, wherein: the display endoscopic image is generated by rotating the endoscopic image based on the angle information, and the channel guide image includes a guide indicating an outlet position of each of the channels, and a first display angle of the display endoscopic image corresponds to a second display angle of the channel guide image.

3. The endoscopic device according to claim 1, wherein the processor is configured to acquire the channel information from the endoscope.

4. The endoscopic device according to claim 1, further comprising:

a memory configured to store the channel information, wherein the processor is configured to acquire the channel information from the memory.

5. The endoscopic device according to claim 4, wherein:

the memory is configured to store respective pieces of channel information on a plurality of endoscopes having different classifications, and the processor is configured to acquire, from the memory, the channel information corresponding to a classification of the endoscope.

6. The endoscopic device according to claim 1, wherein the channel information includes an angle of an outlet position of each of the channels when the display angle of the endoscopic image is a predetermined angle.

7. The endoscopic device according to claim 1, wherein the channel information includes the channel guide image when the display angle of the endoscopic image is a predetermined angle.

8. The endoscopic device according to claim 7, wherein the predetermined angle is any of an angle of 0° or greater.

9. The endoscopic device according to claim 1, wherein the processor is configured to determine whether or not an instruction to rotate the endoscopic image has been received; and in response to determining that the instruction has been received, the processor is configured to acquire the angle information.

10. The endoscopic device according to claim 1, wherein: the at least two channels include a first channel and a second channel, the channel information includes information regarding the first channel and the second channel formed, and the channel guide image is a guide for respective outlet positions of the first channel and the second channel.

11. The endoscopic device according to claim 2, wherein the channel guide image is a guide indicating the outlet position of the channel and a diameter of the channel.

12. The endoscopic device according to claim 1, wherein the processor is configured to:

acquire an operation signal related to an instruction to rotate the endoscopic image, acquire the angle information based on the operation signal, update the display endoscopic image based on the angle information and the endoscopic image, update the channel guide image based on the angle information and the channel information, and output the display image including the updated display endoscopic image and the updated channel guide image.

13. A display image output method comprising:

generating an endoscopic image;

acquiring channel information regarding each of at least two channels formed in an insertion portion of an endoscope;

acquiring angle information regarding a display angle of the endoscopic image;

generating a display endoscopic image by modifying the endoscopic image based on the angle information;

generate a channel guide image separate from the endoscopic image based on both the angle information and the channel information; and generating and outputting a display image including both the display endoscopic image and the channel guide image, wherein the channel information includes information regarding angles of positions of channel outlets of respective ones of the two channels or of the channel guide image when the display angle of the endoscopic image is 0°, and/or information regarding angles of positions of the channel outlets or of the channel guide image when the display angle of the endoscopic image is 180°.

14. A non-transitory computer-readable storage medium storing a computer executable program for causing a computer to perform processing comprising:

generating an endoscopic image;

acquiring channel information regarding each of at least two channels formed in an insertion portion of an endoscope;

acquiring angle information regarding a display angle of the endoscopic image;

generating a display endoscopic image by modifying the endoscopic image based on the angle information;

generate a channel guide image separate from the endoscopic image based on both the angle information and the channel information; and generating and outputting a display image including a-both the display endoscopic image and the channel guide image, wherein the channel information includes information regarding angles of positions of channel outlets of respective ones of the two channels or of the channel guide image when the display angle of the endoscopic image is 0°, and/or information regarding angles of positions of the channel outlets or of the channel guide image when the display angle of the endoscopic image is 180°.

15. An endoscopic system comprising:

an endoscope including:

an insertion portion;

an image pickup device at a distal-end portion of the insertion portion;

at least two channels formed in the insertion portion; and a memory storing channel information regarding the channels, and an endoscopic device including a processor configured to:
  generate an endoscopic image;
  acquire channel information regarding each of at least two channels formed in an insertion portion of an endoscope;
  acquire angle information regarding a display angle of the endoscopic image;
  generate a display endoscopic image by modifying the endoscopic image based on the angle information;
  generate a channel guide image separate from the endoscopic image based on both the angle information and the channel information; and
  generate and output a display image including both the display endoscopic and the channel guide image,
  wherein the channel information includes information regarding angles of positions of channel outlets of respective ones of the two channels or of the channel guide image when the display angle of the endoscopic image is 0°, and/or information regarding angles of positions of the channel outlets or of the channel guide image when the display angle of the endoscopic image is 180°.

16. The endoscopic device according to claim 1, wherein the channel guide image includes a plurality of guides serving as guides for outlet positions of the channels at a point in time after an instruction for endoscopic-image rotation, and the channel information includes information of diameters of the channel outlets.

17. The endoscopic device according to claim 13, wherein the diameters of the channel outlets are displayed on the channel guide image.

18. The endoscopic device according to claim 1, wherein the channel information includes information regarding the angles of positions of channel outlets of respective ones of the two channels when the display angle of the endoscopic image is 0°, and/or information regarding the angles of positions of the channel outlets when the display angle of the endoscopic image is 180°.

19. The display image output method according to claim 13, wherein
  the display endoscopic image is generated by rotating the endoscopic image based on the angle information, and
  the channel guide image includes a guide indicating an outlet position of each of the channels, and
  a first display angle of the display endoscopic image corresponds to a second display angle of the channel guide image.

20. The endoscopic system according to claim 15, wherein
  the display endoscopic image is generated by rotating the endoscopic image based on the angle information, and
  the channel guide image includes a guide indicating an outlet position of each of the channels, and
  a first display angle of the display endoscopic image corresponds to a second display angle of the channel guide image.

* * * * *